United States Patent [19]

Joshi et al.

[11] Patent Number: 5,323,775
[45] Date of Patent: Jun. 28, 1994

[54] DIAGNOSTIC METHOD FOR DETERMINING PRECORNEAL RETENTION TIME OF OPHTHALMIC FORMULATIONS

[75] Inventors: Abhay Joshi, Irvine; David Meadows, Mission Viejo; Jerry Paugh, Costa Mesa, all of Calif.

[73] Assignee: Allergan, Inc., Irvine, Calif.

[21] Appl. No.: 759,530

[22] Filed: Sep. 13, 1991

[51] Int. Cl.⁵ .................. A61B 5/00; A61B 6/00; A61B 19/00
[52] U.S. Cl. .................. 128/633; 128/664; 128/898
[58] Field of Search .................. 351/206, 214, 241; 128/633, 634, 665, 661.06, 898; 424/78.04

[56] References Cited

U.S. PATENT DOCUMENTS

| | | | |
|---|---|---|---|
| 4,003,991 | 1/1977 | Krahn et al. | 424/78.04 X |
| 4,120,949 | 10/1978 | Bapatta et al. | 424/78.04 |
| 4,407,792 | 10/1983 | Schoenwald et al. | 424/78.04 X |
| 4,409,205 | 10/1983 | Shively | 424/78.04 |
| 4,412,543 | 11/1983 | Vassiliadis et al. | 128/665 X |
| 4,474,751 | 10/1984 | Haslam et al. | 424/78.04 X |
| 4,540,568 | 9/1985 | Trager et al. | 424/78.04 |
| 4,573,778 | 3/1986 | Shapiro | 128/633 X |
| 4,594,326 | 6/1986 | Wade | 128/633 X |
| 4,597,965 | 7/1986 | Holly | 424/78.04 X |
| 4,702,576 | 10/1987 | Magnante | 351/214 |
| 4,711,540 | 12/1987 | Yoshino et al. | 128/633 X |
| 4,711,541 | 12/1987 | Yoshino et al. | 128/633 X |
| 4,744,980 | 5/1988 | Holly | 424/78.04 |
| 4,842,401 | 6/1989 | Maurice | 128/663 X |
| 4,852,987 | 8/1989 | Lohmann | 128/633 X |
| 4,863,261 | 9/1989 | Flammer | 128/633 X |
| 4,883,351 | 11/1989 | Weiss | 128/633 X |
| 4,883,658 | 11/1989 | Holly | 424/78.04 X |
| 4,895,159 | 1/1990 | Weiss | 128/633 X |
| 4,966,773 | 10/1990 | Gressel et al. | 424/78.04 X |
| 5,025,785 | 6/1991 | Weiss | 128/633 |
| 5,171,526 | 12/1992 | Wong et al. | 424/78.04 X |

FOREIGN PATENT DOCUMENTS 8602548 5/1986 World Int. Prop. O. ........ 424/78.04

OTHER PUBLICATIONS

International Jove Pharmaceutics vol. 61, No. 1, 2, Jun. 11, 1990 Amsterdam investigative Ophthamology vol. 14/12 Dec. 1975 pp. 887-902.
Analytical Biochemistry vol. 130, 1983 U.S. pp. 287-294.
"The Instilled Fluid Dynamics and Surface Chemistry of Polymers in the Preocular Tear Film", Benepeitto, P. A. et al. Investigative Opthalmology p. 887 Dec. 1975.
"Evaluation of Viscous Ophalmic Vehicles Containing Carboner by Slit-Lamp Fluorophotometry in Humans", Ludwig, A et al. International Jo. of Pharmaceutics p. 15 vol. 61 1990.
"The Effect of Viscosity of the Vehicle on the Penetration of Fluorescein into the Human Eye", Adler, C. A. et al. Exptl Eye Res p. 34 vol. 11, 1971.
"The Evaluation of Viscous Ophthalmic Vehicles by Slit Lamp Fluorophotometry in Humans", Ludwig A. et al. Intl. Jo. of Pharaceutics p. 95 vol. 54, 1989.
"Scintgraphic Assesment of an Opthalmic Gelling Vehicle in Man and Rabbit".
Greaves, J. L. et al. Current Eye Research, p. 415 vol. 9 No. 5, 1990.

*Primary Examiner*—Randall L. Green
*Assistant Examiner*—Elizabeth M. Burke
*Attorney, Agent, or Firm*—Walter A. Hackler

[57] ABSTRACT

Apparatus and method for measuring ophthalmic formulation retention on the surface of an eye include dissolving a fluorescent macromolecule in an ophthalmic formulation to form a fluorescently labelled formulation; topically administering the fluorescently labelled formulation to an eye, said fluorescently labelled formulation forming a thin film on the eye surface. Apparatus is provided for illuminating the eye to cause fluorescence of the fluorescently labelled formulation as the fluorescently labelled formulation thin film is eliminated from the eye by normal blinking and lacrimation; and for measuring fluorescence from the thin film as a function of time.

4 Claims, 3 Drawing Sheets

DIAGNOSTIC METHOD FOR DETERMINING PRECORNEAL RETENTION TIME OF OPHTHALMIC FORMULATIONS

The present invention generally relates to slit lamps for eye examination and more particularly, the present invention is directed to a specially modified slit lamp and the use thereof for continuously monitoring the emitted fluorescence in topically administered ophthalmic formulations.

Measurement of the retention time of ophthahic formulations in the eye is important in the optimization of new ophthahic dosage forms and droppable gel systems containing pharmaceutical agents for treatment of many eye conditions in addition to contact lens wetting, wound healing and sustained drug release.

Heretofore one of the most common methods utilized in making retention time measurements includes the use of sodium fluorescein which is added to an ophthahic formulation and instilled into the cul-de-sac of an animal or human subject to form a thin film over the surface of the eye. The fluorescence signal is then monitored with time using a slit lamp fhorophotometer. Unfortunately, this sodium fluorescein is rapidly eliminated from the film by two predominant mechanisms: It is washed out of the eye by new lacrimal secretions or, being a relatively small molecule, it diffuses into the ocular tissue and is thereafter absorbed into the systemic circulation. The second type of elimination of the sodium fluorescein from the thin film is a source of error in retention time measurements as it is difficult to distinguish between fluorescence of the thin film from fluorescence from the tissue.

In an effort to prevent fluorescein diffusion, attempts have been made to increase the viscosity of the instilled optical formulations causing the fluorescein to be retained longer in the precorneal tear film (PTF). (See Benedetto, D. A.; Shah, D. O.; and Kaufman, H. E., "The instilled fluid dynamics and surface chemistry of polymer in the preocular tear film," *Investigative Ophthalmology,* Dec. 1975.) While the referenced article shows that fluorescein retention increases by a moderate amount with increased viscosity of the vehicle, diffusion of fluorescein into the ocular tissue actually plays a larger role in the elimination of fluorescein from the PTF as the retention time of the vehicle increases. Also, it has been reported by the Benedetto et al. reference that there is little understanding of the relative importance of the role each physicochemical property of the polymer plays on the retention properties of the polymer solutions, and it is probable that in each case different properties assume major importance in determining the overall retention times.

Therefore, it is not practical to add to proposed or existing eye formulations viscosity builders in order to drastically reduce fluorescein diffusion when eye formulation retention time is to be measured and evaluated. It is also well-known that increasing the viscosity of eye formulation can result in eye irritation and/or blurred vision. Hence, subjects typically react by forceful blinking, squeezing the formulation out of the conjunctival sac, and accelerating the drainage of the fluorescein tracer.

This is particularly true in comparison testing of eye formulations since, as reported, added viscosity builders would not uniformly enhance the properties of the eye formulations, thus making comparative testing not very reliable.

It is important to realize that with or without such viscosity builders, the diffusion rate of fluorescein out of the PTF severely limits the accuracy of retention time measurement.

Because there is no bonding between fluorescein and polymers, the fluorescein diffuses freely in the viscous vehicle (Ludwig, A.; Unler, N., and VanOoteghem, M., "Evaluation of viscous ophthalmic vehicles containing carbomer by slit-lamp fluorophotometry in humans," *International Journal of Pharmaceutics,* pp. 15–25, Vol. 61, 1990. And while the carbomer of specific investigation in the Ludwig article increased the ocular retention of sodium fluorescein, the retention time was less than ten minutes.

Other methods for measuring the retention times of ophthalmic formulations in the eye include gamma scintigraphy. However, these methods involve the use of radioisotopes and therefore necessitate expensive equipment and a laboratory suited for the handling of radioactive compounds. Because of the specialized equipment needed to conduct such testing, it is not cost-effective for a typical laboratory to make measurements on their ocular formulations. Also, typically, the radioactive compounds have low molecular weights so they too may freely diffuse out of the viscous vehicle and into ocular tissue or be deposited on the lid margins that will result in erroneous retention measurements.

Hence there is a need for an apparatus and method suitable for use by independent laboratories in making important quantitative measurements in their development of new ophthalmic dosage forms and formulations. The apparatus and method of the present invention are suited for such application and in fact the optical detection apparatus of the present invention can be easily mounted or dismounted from existing slit lamps. This has a distinct advantage for clinicians who wish to evaluate the performance of a specific ophthalmic formulation for a particular patient with disease. Because limited additional equipment is required to make the measurements, the incremental cost to clinical practice is minimal.

SUMMARY OF THE INVENTION

Apparatus for the measurement of ophthahic formulation retention on the surface of the eye, in accordance with the present invention, generally includes means for supporting the subject and enabling access of light to the subject eye, along with means for illuminating the subject eye. Importantly, the means for illuminating the subject eye comprises filter means for causing illumination of the subject eye with light of a selected frequency range in order to cause fluorescence of a fluorescent formulation topically administered to the surface of the subject's eye and forming a thin film thereover. As will be hereinafter described in greater detail, the filter means may be installed in a conventional slit lamp, thereby enabling the apparatus of the present invention to be fabricated from a conventional slit lamp system, thus reducing the overall cost of the apparatus.

In addition, the apparatus of the present invention includes means for measuring the fluorescent light from the thin film with such means including filter means for preventing the measurement of background light signals that can cause "noisy" fluorescence signals.

A method in accordance with the present invention for measuring ophthahic formulation retention on the surface of an eye generally includes the steps of dissolving a fluorescent macromolecule in an ophthahic formulation to form a fluorescently labelled formulation and thereafter topically administering the fluorescently labelled formulation to an eye, whereupon the fluorescently labelled formulation forms a thin precorneal film on the eye surface.

Thereafter, the eye is illuminated to cause fluorescence of the fluorescently labelled formulation as the fluorescently labelled formulation thin film is eliminated from the eye by normal blinking and lacrimation. During this time, the fluorescence from the thin film is measured.

More particularly, the method in accordance with the present invention may include the step of dissolving a fluorescent macromolecule in the ophthalmic formulation, the fluorescent macromolecule having sufficiently large molecular weight to prevent diffusion of the same out of the thin film during illumination of the eye and thereby insuring measurement of fluorescence from the preconheal thin film only. Further, the fluorescent molecule may have a molecular weight greater than about 2,000 Daltons in order to prevent diffusion of the fluorescent macromolecule out of the thin film. Diffusion into the ocular tissue is prevented by the large size of the fluorescent macromolecule, and preferential diffusion of the macromolecule out of the thin film is prevented by entanglements between the macromolecule and the large molecular weight excipients in the formulation.

In one embodiment of the present invention, the method further includes the step of covalently attaching a fluorescent compound having a molecular weight of less than about 2,000 Daltons to a compound to form a fluorescent macromolecule.

In combination, the present invention also encompasses a system for measuring the retention of ophthalmic formulations on the surface of an eye which includes at least one fluorescently labelled ophthalmic formulation containing a fluorescent macromolecule having molecular weight greater than about 2,000 Daltons, means for illuminating the eye and causing fluorescence of the fluorescently labelled ophthalmic formulation when the same is topically administered to an eye, and means for measuring the fluorescence from the topically administered fluorescently labelled ophthalmic formulation.

BRIEF DESCRIPTION OF THE DRAWINGS

The advantages and features of the present invention will appear from the following description when considered in conjunction with the accompanying drawings in which.

DETAILED DESCRIPTION OF THE DRAWINGS

Figure 1:
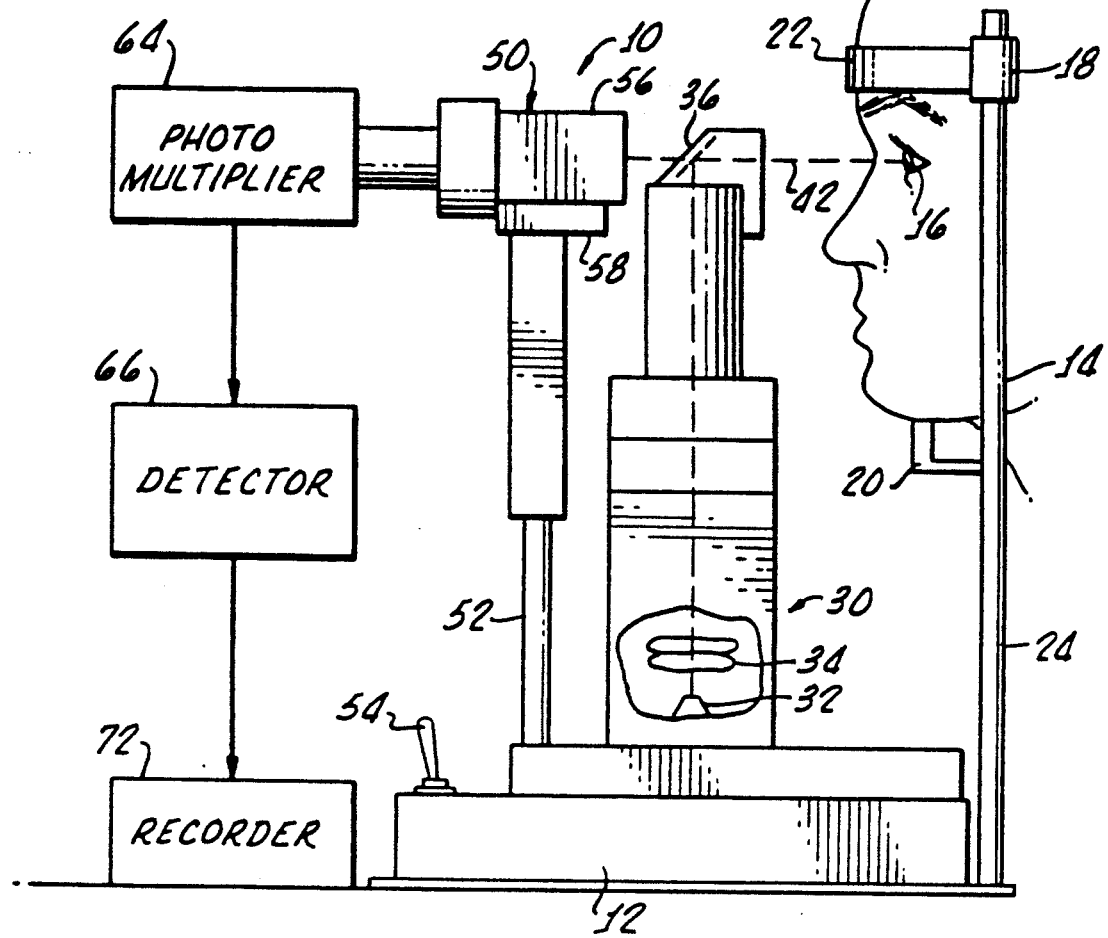
FIG. 1 is a schematic of the apparatus in accordance with the present invention generally showing a support for a subject enabling illumination of an eye with a light source to cause fluorescence of a fluorescent formulation disposed on the surface of an eye along with a receiver for measuring the fluorescence emitted from the eye.

Turning now to FIG. 1, there is shown apparatus 10 in accordance with the present invention which generally includes a base 12 and a subject support assembly 14 attached thereto which provides means for supporting a subject and enabling light access to the subject's eye 16.

It should be appreciated that the support assembly 14 may be of any conventional type and include members 18 conventionally adapted for the support of either a human or animal head and include a chin support 20 or the like. In the case of a human subject, the support assembly 14 may include a forehead support 22 and a post 24 for supporting the chin support 20 at a proper elevation.

A light projection assembly 30 includes a light source 32 and lenses 34 along with a mirror 36 which in combination provide means for illuminating the subject's eye 16 with light of a selected frequency range in order to cause fluorescence of a fluorescent formulation topically administered to the surface of the subject's eye. The transmission characteristics of the filter, of course, are dependent upon the excitation frequency of the fluorescent compound and, as an example, for use with the fluorescent compounds hereinafter discussed, an appropriate excitation interference filter, such as a 490 nm center wavelength with a 10 nm bandpass that was custom made by Omega Optical of Brattleboro, Vt. A standard optical slit lamp such as a Nikkon FS II slit lamp may be modified with the appropriate filters 34.

Figure 2:
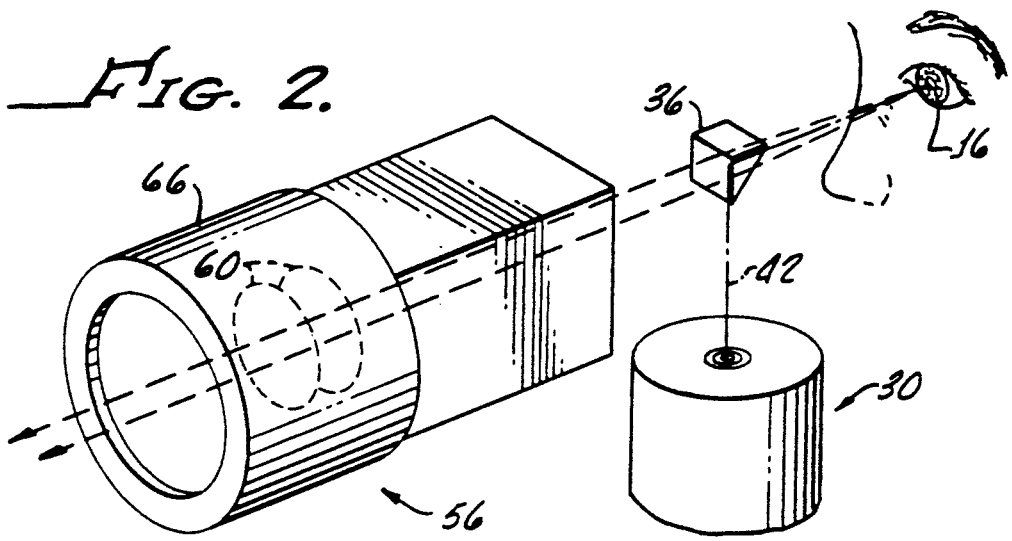
FIG. 2 is a schematic representation of a receiver of fluorescent light from a subject eye depicting a lens arrangement therein.

It should be appreciated that the filters 34 should be carefully selected in order to eliminate stray excitation light which can significantly limit the sensitivity of the instrumentation. As illustrated in FIGS. 1 and 2, the excitation light 42 is directed to the subject's eye 16 for excitation of the fluorescently labelled ophthalmic formulation topically administered to the subject's eye 16. Upon excitation, fluorescence occurs whereupon unpolarized light of a different wavelength is emitted from the ophthalmic formulation with such light 42 being directed through the mirror 36 into a viewing assembly 50 which includes an arm 52, upstanding from the base 12, which is movable by means of a control lever 54 to adjust the emitted light 42 into an objective system 56 supported by a fixture 58 connected to the arm 52. The objective system 56 is adapted to support emission filters 60, such as a 530 nm center wavelength with a 20 nm bandpass that was custom made by Omega Optical. A photomultiplier tube 64 such as Oriel Corporation, Stratford, Conn., Model No. 77349 may be attached to a housing 66 of the objective system.

In turn, the photomultiplier tube 64 is interconnected with a conventional detector 66 such as an Oriel Model No. 7070 which may be connected to a recorder 72 in a conventional manner. In combination, the objective system 56 lenses 60, photomultiplier tube 64, detector 70, and recorder 72 provide means for measuring the fluorescent light from the thin precorneal tear film (not shown) and the filters 60 further provide means for preventing measurable light of nonfluorescent light frequency from reaching the photomultiplier tube 64.

Ophthalmic formulations in accordance with the present invention for measuring ophthalmic formulation retention in an eye may include a pharmaceutical agent in an aqueous vehicle for an eye and a fluorescent macromolecule having a molecular weight greater than about 2,000 Daltons that is dissolved in the vehicle. A large number of macromolecules are suitable for combination with the pharmaceutical agent and include FITC-Dextran, TRITC-Dextran, Phycobiliproteins and FITC-labelled synthetic polymers or proteins. These polymers are available from commercial suppliers such as Molecular Probes, Eugene, Oreg.

The fluorescently labelled solution, when topically administered to the eye 16, is effectively spread evenly over the surface of the eye by the blinking mechanism. This fluorescent film is gradually eliminated from the eye through blinking and tear secretions. Since the molecular weight of the tracer is sufficiently large, diffusion of the tracer into ocular tissue is completely eliminatede. Hence, the fluorescent label is localized in the pre-corneal tear film which provides for superior spatial resolution of fluorescence measurements.

Thus, the system, which includes the ophthalmic formulation and the apparatus hereinbefore described, is able to obtain a very accurate quantitative measurement of the ophthalmic formulation that resides on the surface of an eye and the rate at which it is removed over time. The removal of the ophthalmic formulation is attributed primarily to normal blinking and lacrimation of the eye and not diffusion of the fluorescent label from the thin film on the eye 16. It should be appreciated that the fluorescent macromolecule has a molecular weight of greater than 2,000 Daltons and preferably as much as 2,000,000 Daltons such as phycobiliproteins. Alternatively, the fluorescent macromolecule may be a combination of a fluorescent compound such as fluorescein isothiocyanate having a molecular weight of less than about 2,000 Daltons bonded to a compound such as Dextran having a molecular weight of 70,000 Daltons so that the combined weight of the molecule, which is preferably covalently bonded, is greater than 2,000 Daltons. Not only does the large size of the tracer prevent diffusion into the ocular tissue, but the tracer macromolecule will be entangled with any other macromolecules in the ophthalmic formulation in order to prevent preferential diffusion of the tracer out of the tear film.

Figure 3:
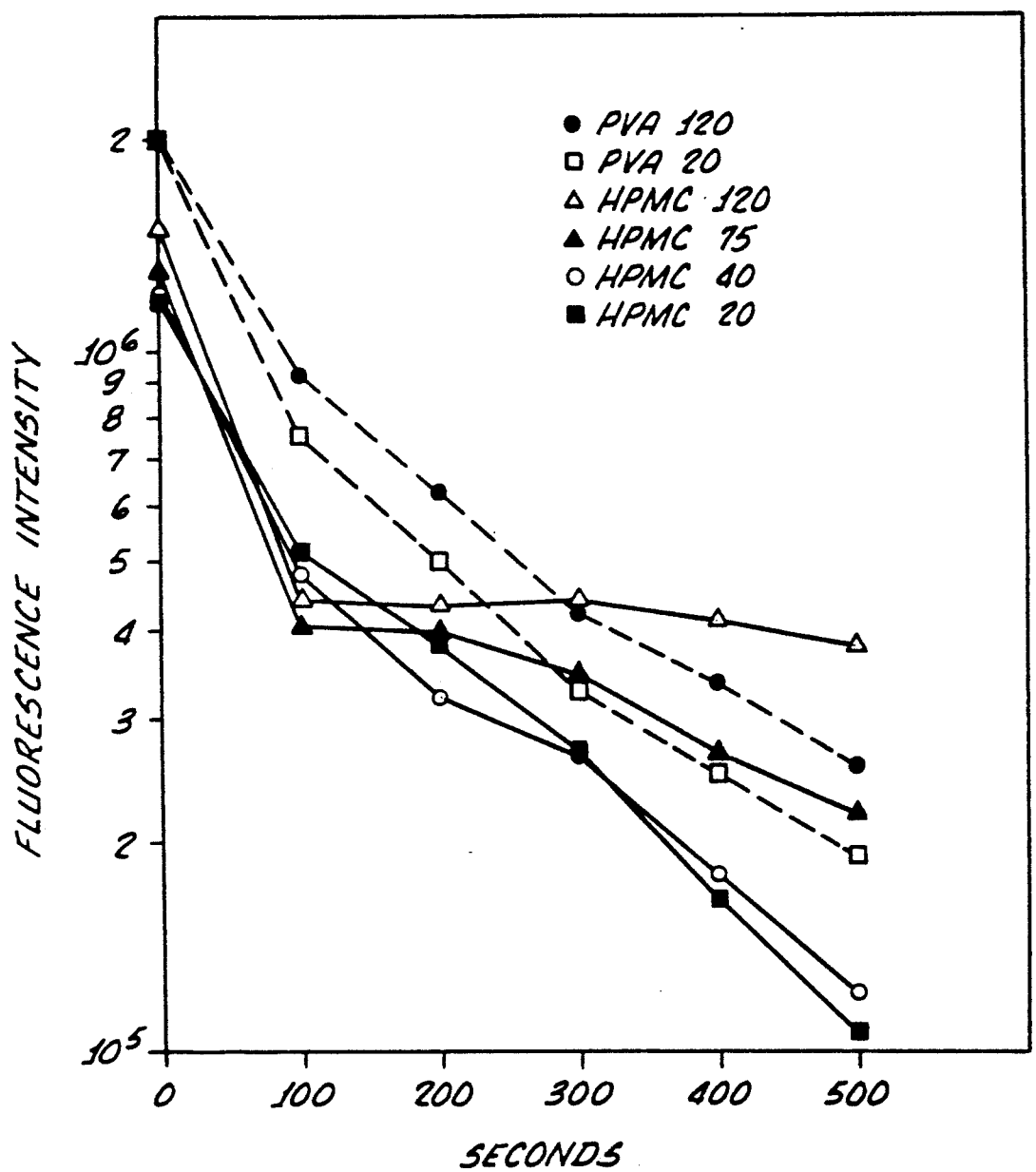
FIG. 3 is a plot showing the effect of varying viscosity of hydroxypropyhethyl cellulose (HPMC) and polyvinyl alcohol (PVA) on fluorescein retention in the PTF.

Heretofore measurements of retention time have been limited in duration, in part, due to the diffusion of low molecular weight tracers from the PTF. As shown in FIG. 3, as reported by Benedetto, Shah and Kaufman in Investigative Ophthalmology, December 1975, if the low molecular weight tracer sodium fluorescein is used, then unless the viscosity of the vehicle is greater than about 20 cp, the retention times are less than 10 minutes. As hereinabove pointed out, greater retention time can often be achieved with higher viscosity formulations, but if the viscosity is too large, then it is often accompanied by blurred vision and eye irritation.

Figure 4:
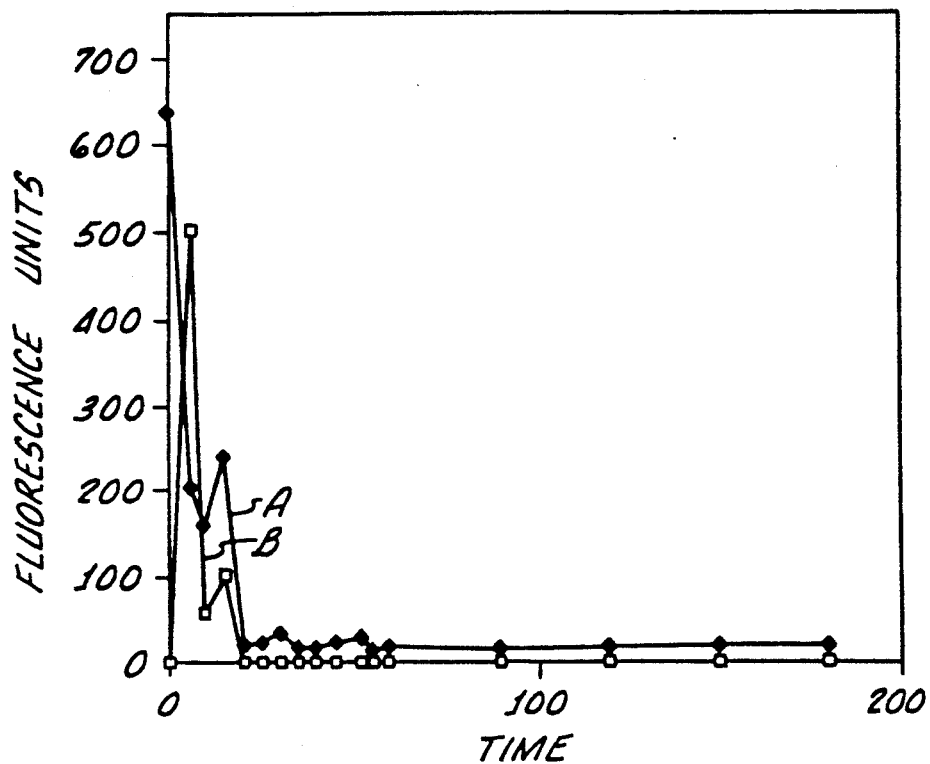
FIGS. 4-5 are plots showing the measurement of retention times of ophthahic formulations in rabbits for up to 175 minutes enabled by the fluorescent macromolecules of the present invention.
Figure 5:
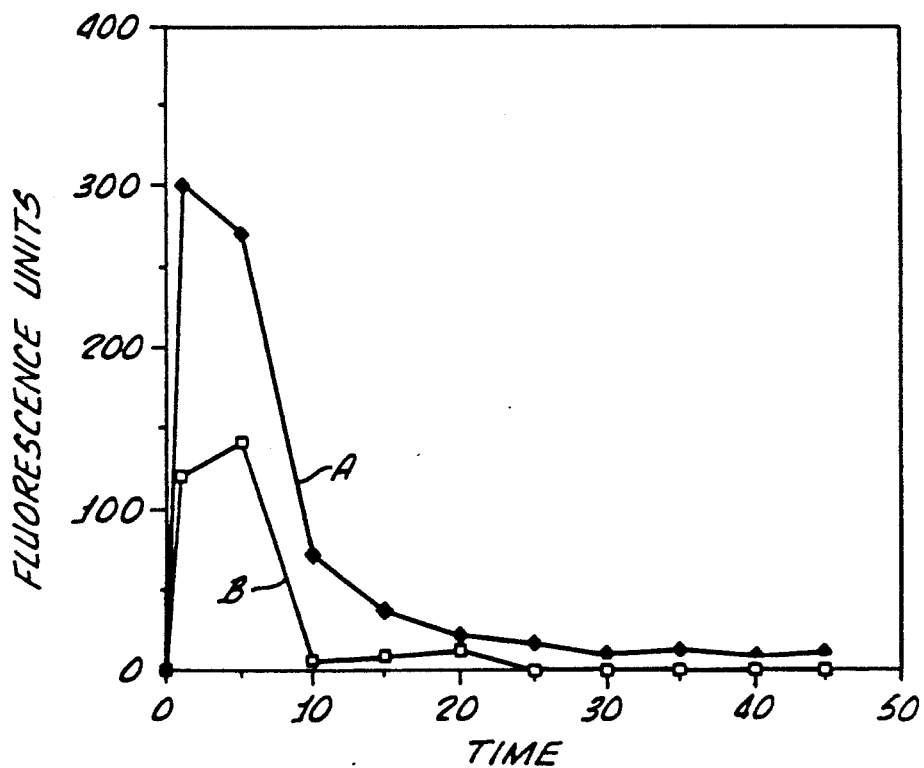

As shown in FIGS. 4-5 for New Zealand albino rabbits, the apparatus and method of the present invention are suitable for retention time measurement of up to 175 minutes by increasing the viscosity of the ophthalmic formulation. Formulations A-B of FIG. 4 were made with 0.1%, by weight, FITC-Dextran (70,000 Daltons) and had viscosities of 5,000 cp and 300 cp, respectively, which are unaffected by the addition of the FITC Dextran. Comparing the retention times shown in FIGS. 3 and 4, it can be seen that the macromolecule tracer of the present invention does not require a high viscosity formulation or vehicle in order to maintain its presence in the PTF, thus providing a reliable long term measurement of retention time through detection of emitted fluorescence.

Hence, the method of the present invention is ideally suited for the quantitative determination of retention times for ocular formulations because the tracer does not preferentially diffuse out of the formulation and therefore does not give erroneous measurements.

FIG. 5 illustrates the usefulness of the present invention when comparing the performance of various formulations. Comparison of curve A (viscosity equals 1,000 cp) with curve B (viscosity equals 10 cp), a commercially available artificial tear, shows that the higher viscosity formulation is definitely retained longer in the eye.

As hereinabove described, a fluorescent macromolecule suitable for use with the apparatus and formulations of the present invention may include commercially available fluorescent tracers having a molecular weight greater than about 2,000 Daltons. However, a fluorescent molecule in accordance with the present invention may also be produced by covalently attaching a fluorescent compound having a molecular weight of less than about 2,000 Daltons to a compound having a molecular weight sufficient to produce a macromolecule with a molecular weight greater than 2,000 Daltons. For example,

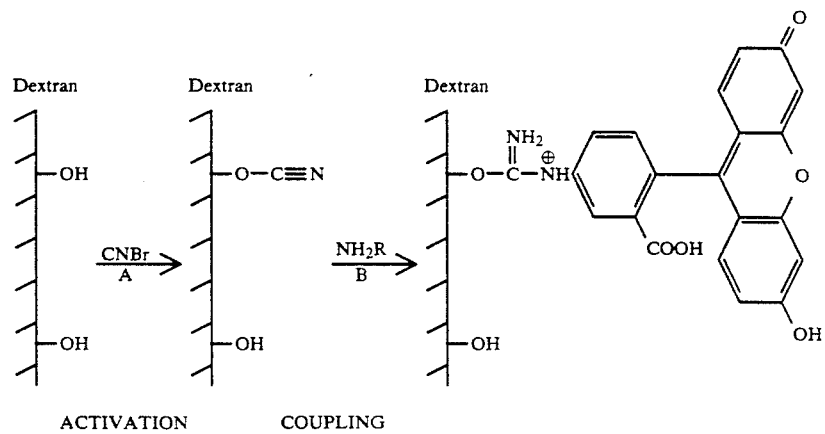

| | |
|---|---|
| REACTION A: | Dissolve 20 mg Dextran in water adjusted to pH 11 with 0.2 M NaOH.<br>Dissolve 10 mg cyanogen bromide in 0.2 ml water.<br>Mix Dextran and cyanogen bromide solutions together and maintain pH 11 for 5 minutes.<br>Desalt activated Dextran using 1 × 20 cm column of Sephadex G-50 in 0.2 M sodium borate at pH 8.0. |
| REACTION B: | Pool Dextran-containing fractions.<br>Immediately react pooled Dextran samples with 2 mg of fluorescein (R) amine.<br>Let mixture react for 12-18 hours.<br>Separate fluorescein-Dextran from unreacted fluorescein amine using Sephadex G-50 1 × 20 cm column equilibrated in phosphate buffered saline. |

From: Glabe, C. G.; Harty, P. K.; and Rosen S. D., "Preparation and Properties of Fluorescent Polysaccharides," *Analytical Biochemistry*, 130 (1983) 287-294.

While fluorescent macromolecules having a molecular weight of less than 2,000 Daltons may be useful, it has been found that diffusion of the macromolecule into ocular tissues is minimal at molecular weights greater than about 2,000 Daltons which enables the measurement of retention time as long as the ophthalmic formulation is retained in the precorheal region.

Separately and in combination with the hereinabovedescribed apparatus 10, a method for measuring ophthalmic formulation retention on the surface of an eye includes the steps of dissolving a fluorescent macromolecule, such as FITC-Dextran, in an ophthalmic formulation to form a fluorescently labelled formulation having a concentration of 0.1% by weight of said fluorescent molecule. Thereafter, the fluorescently labelled formulation is topically administered to the eye 16 with the fluorescently labelled formulation forming a thin film on the eye surface. The light source 30 is used to illuminate the eye as the fluorescently labelled formulation contained in the thin film is eliminated from the eye by normal blinking and lacrimation and the objective system 56, with multiplier tube 64 and detector 70 are utilized for measuring the fluorescence from the thin film as a function of time.

In the case where the macromolecule is not fluorescent, the method of the present invention may further comprise the step of covalently attaching a fluorescent compound having a molecular weight of less than about 2,000 Daltons to a compound to form the fluorescent molecule having a molecular weight of greater than 2,000 Daltons, as hereinabove described.

The apparatus 10 in combination with a fluorescent macromolecule such as FITC-Dextran has provided a superior method for obtaining accurate quantitative measurements of precorneal retention times for ocular formulations. Its usefulness lies in the comparison of newly formulated ocular formulations with commercially available products or in the process of screening new formulations. Typical results of such comparison measurements are shown in FIG. 4 which is illustrative of the fact that the use of a fluorescently labelled macromolecule can measure retention times of up to 175 minutes.

In this procedure, the samples to be tested are prepared with an appropriate amount of fluorescent tracer material and instilled into the cul-de-sac of the animal or human subject. A baseline measurement is made prior to sample installation by adjusting the sensitivity of the detector system to the appropriate level expected in the experiment and focussing the beam of the slit lamp on the precorneal tear film of the subject.

The signal intensity of the baseline reading can then be subtracted using instrumental controls in a conventional manner. The light intensity and beam width and height are also set to prescribed values. Following the adjustments for the baseline, a sample is instilled in the eye and immediately after the sample has been evenly spread over the surface of the eye with several quick blinks, a time zero measurement is taken. This measurement is made by quickly focussing the beam of the slit lamp on the precorneal tear film and reporting the photomultiplier signal on the printout from the recorder 72. This procedure can be repeated as often as required until the signal has returned to the baseline indicating all of the sample has been eliminated from the eye.

Although there has been hereinabove described a specific arrangement and method for measuring ophthalmic formulation retention on the surface of an eye in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A method for measuring retention times of an ophthalmic formulation on a surface of an eye, said method comprising the steps of:

dissolving a fluorescent macromolecule in an ophthalmic formulation to form a fluorescently labelled formulation;

topically administering the fluorescently labelled formulation to an eye, said fluorescently labelled formulation forming a thin film on the eye surface;

illuminating the eyes to cause fluorescence of the fluorescently labelled formulation as the thin film is eliminated from the eye by normal blinking and lacrimation; and measuring fluorescence from the thin film as a function of time.

2. The method according to claim 1 wherein the step of dissolving a fluorescent macromolecule comprises dissolving, in said ophthalmic formulation, a fluorescent macromolecule having sufficient molecular weight in order to prevent diffusion of the fluorescent macromolecule out of the thin film during an experimentation period and enabling measurement of formulation retention times of more than 30 minutes.

3. The method according to claim 1 wherein the step of dissolving a fluorescent macromolecule comprises dissolving, in said ophthalmic formulation, a fluorescent macromolecule having a molecular weight greater than about 2,000 Daltons in order to prevent diffusion of the fluorescent macromolecule out of the thin film during illumination of the eye and enable measurement of formulation retention times of at least 175 minutes.

4. The method according to claim 1 further comprising the step of covalently attaching a fluorescent compound having a molecular weight of less than about 2,000 Daltons to a compound to form the fluorescent macromolecule.

* * * * *